United States Patent [19]

Polisson et al.

[11] Patent Number: 5,147,794
[45] Date of Patent: Sep. 15, 1992

[54] **TYPE II RESTRICTION ENDONUCLEASE OBTAINABLE FROM *KLUYVERA ASCORBATA* AND A PROCESS FOR PRODUCING THE SAME**

[75] Inventors: Carol Polisson, Reading; Janet M. Barsomian, Georgetown, both of Mass.

[73] Assignee: New England Biolabs, Inc., Beverly, Mass.

[21] Appl. No.: 557,394

[22] Filed: Jul. 23, 1990

[51] Int. Cl.$^5$ .......................... C12N 9/22; C12N 15/00
[52] U.S. Cl. ................................. 435/199; 435/172.3
[58] Field of Search ............................ 435/199, 172.3

[56] References Cited

U.S. PATENT DOCUMENTS

4,975,376 12/1990 Bolton ................................. 435/199

FOREIGN PATENT DOCUMENTS

1093413 3/1986 European Pat. Off. .

OTHER PUBLICATIONS

Endow et al., J. Mol. Biol. 112:521 (1977).
Waalwijk et al., Nucleic Acids Res. 5:3231 (1978).
Gingeras et al., Proc. Natl. Acad. Sci. U.S.A. 80:402 (1983).
Mann et al., Gene 3:97-112 (1979).
Kosykh et al., Molec. Gen. Genet. 178:717-719 (1980).
Walder et al., Proc. Nat. Acad. Sci. USA 78:1503-1507 (1981).
Bougueleret et al., Nucleic Acids Res. 12:3659-3676 (1984).
Theriault and Roy, Gene 19:355-359 (1982).
Blumenthal et al., J. Bacteriol. 164:501-509 (1985).
Howard et al., Nucleic Acids Res. 14:7939-7951 (1988).
Wilson et al., Gene 74:281-289 (1988).
Wilson, Trends in Genetics 4:314-318 (1988).
Lunnen et al., Gene 74:25-32 (1988).
Chandrasegeran et al., Structure and Expression, vol. I, pp. 149-156, Adenine Press (1988).
Brooks et al., Gene 74:13 (1988).

*Primary Examiner*—John J. Doll
*Assistant Examiner*—Suzanne Ziska
*Attorney, Agent, or Firm*—David G. Conlin; Gregory D. Williams; David S. Resnick

[57] ABSTRACT

The present invention provides a novel restriction endonuclease obtainable from the bacterium *Kluyvera ascorbata*, hereinafter referred to as "KasI", which endonuclease:

(1) recognizes the base sequence in a double-stranded DNA molecule as shown below, $$5'-G\!\!\downarrow\!\!GCGCC-3'$$
$$3'-CCGCG\!\!\uparrow\!\!G-5'$$

(wherein C and G represent cytosine and guanine, respectively), (2) cleaves said sequence in th4e phosphodiester bonds between G and G as indicated with the vertical arrows; and (3) cleaves double-stranded pUC, M13mp18, and lambda DNA in one position, PhiX172, and T7 DNA in two positions, and Adeno2 DNA at 20 positions, while not cleaving SV40 DNA.

The present invention further provides a recombinant DNA encoding the KasI restriction endonuclease and modification methylase obtainable from *K. ascorbata*, and methods for the production of the recombinant DNA encoding those enzymes. Methods for producing the KasI restriction endonuclease and modification methylase in substantially pure form are also provided.

5 Claims, 2 Drawing Sheets

TYPE II RESTRICTION ENDONUCLEASE OBTAINABLE FROM *KLUYVERA ASCORBATA* AND A PROCESS FOR PRODUCING THE SAME

BACKGROUND OF THE INVENTION

The present invention relates to a new Type II restriction endonuclease, KasI, obtainable from *Kluyvera ascorbata*, to recombinant DNA encoding the KasI restriction endonuclease and modification methylase, and to methods for the production of these enzymes from said recombinant DNA.

Many bacteria contain systems which guard against invasion of foreign DNA. Bacterial cells contain specific endonucleases that make double-strand scissions in invading DNA unless the DNA has been previously modified, usually by the corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Three distinct types of R-M systems have been characterized on the basis of the subunit compositions, co-factor requirements, and type of DNA cleavage. Type I R-M systems are the most complex. The endonuclease typically contains three different types of subunits and require $Mg^{++}$, ATP, and S-adenosyl-methionine for DNA cleavage. Their recognition sites are complex, and DNA cleavage occurs at non-specific sites anywhere from 400-7000 base pairs from the recognition site. Type III R-M systems are somewhat less complex. The endonuclease of type III R-M systems contain only two types of subunits, and although $Mg^{++}$ and ATP are required for DNA cleavage, S-adenosyl-methionine stimulates enzymatic activity without being an absolute requirement. DNA cleavage occurs distal to the recognition site by about 25-27 base pairs.

Type II R-M systems are much simpler than either types I or III. The endonuclease only contains one subunit, and only $Mg^{++}$ is required for DNA cleavage. Moreover, the DNA cleavage site occurs within or adjacent to the enzyme's recognition site. It is this class of restriction endonucleases that has proved most useful to molecular biologists.

Bacteria usually possess only a small number of restriction endonucleases per species. The endonucleases are named according to the bacteria from which they are derived. Thus, the species *Haemophilus aeovotius*, for example synthesizes three different restriction endonucleases, named Hae I, Hae II and Hae III. These enzymes recognize and cleave the sequences (AT)GGCC(AT), PuGCGCPy and GGCC respectively. *Escherichia coli* RY13, on the other hand, synthesizes only one enzyme, EcoR I, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4-6 nucleotides in length. More recently, recognition endonucleases having recognition sequences of 7-8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes." Some restriction endonucleases have degenerate or relaxed specificities in that they can recognize multiple bases at the same positions. HaeIII, which recognizes the sequence GGCC is an example of restriction endonuclease having a symmetrical relationship, while HaeII, which recognizes the sequence PuGCGCPy, typifies restriction endonucleases having a degenerate or relaxed specificity. Endonucleases with symmetrical recognition sites generally cleave symmetrically within or adjacent to the recognition site, while those that recognize asymmetric sites tend to cut at distance from the recognition site, typically from about 1 to 18 base pairs away from that site.

The second component of bacterial R-M systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or more of the nucleotides within the sequence by the addition of a methyl group. Following methylation, the recognition sequence is no longer bound or cleaved by the corresponding restriction endonuclease. The DNA of a bacterial cell is always fully modified by virtue of the activity of its modification methylase, and it is therefore completely insensitive to the presence of the endogenous restriction endonuclease. It is only unmodified, and therefore identifiably foreign DNA that is sensitive to restriction endonuclease recognition and attack.

More than 1,000 different restriction endonucleases have been isolated from bacterial strains, and many share common specificities. Restriction endonucleases which recognize identical sequences are called "isoschizomers." Although the recognition sequences of isoschizomers are the same, they may vary with respect to site of cleavage (e.g., XmaI v. SmaI Endow et al., *J. Mol. Biol.* 112:521 (1977) Waalwijk et al., *Nucleic Acids Res.* 5:3231 (1978)) and in cleavage rate at various sites (XhoI v. Pae R7I Gingeras et al., *Proc. Natl. Acad. Sci U.S.A.* 80:402 (1983)).

With the advent of genetic engineering technology, it is now possible to clone genes and to produce the proteins and enzymes that they encode in greater quantities than are obtainable from their natural sources by conventional purification techniques.

Type II restriction-modification systems are being cloned with increasing frequency. Four methods are being used to clone R-M systems into *E. coli*: (1) subcloning of natural plasmids; (2) selection based on phage restriction; (3) selection based on vector modification; and (4) multi-step isolation.

The first cloned systems used bacteriophage infection as a means of identifying or selection restriction endonuclease clones (HhaII: Mann, et al., *Gene* 3:97-112, (1978); EcoRII: Kosykh, et al., *Molec. Gen. Genet.* 178:717-719, (1980); PstI: Walder, et al., *Proc. Nat. Acad. Sci. USA* 78:1503-1507, (1981)). Since the presence of R-M systems in bacteria enables them to resist infection by bacteriophages, cells that carry cloned R-M genes can, in principle, be selectively isolated as survivors from libraries that have been exposed to phage. This method has been found, however, to have only limited value. Specifically, it has been found that cloned R-M genes do not always manifest sufficient phage resistance to confer selective survival.

Subcloning of natural plasmids involves transferring systems initially characterized as plasmid-borne into *E. coli* cloning plasmids (EcoRV: Bougueleret, et al., *Nucleic Acids Res.* 12:3659–3676, (1984); PaeR7: Gingeras and Brooks, *Proc. Natl. Acad. Sci. USA* 80:402–406, (1983); Theriault and Roy, *Gene* 19:355–359, (1982); PvuII: Blumenthal, et al., *J. Bacteriol.* 164:501–509, (1985)). In this approach the plasmids are purified prior to digestion and ligation, so reducing the complexity of the source DNA. Isolating the system then involves sub-cloning and characterizing libraries and performing selections.

Vector modification, the most successful approach to date, is predicated on the assumption that the restriction and modification genes of a particular Type II system are linked and are expressed sequentially, methylase and then endonuclease. Thus, in a population of methylase positive clones, some clones should also carry the corresponding endonuclease gene. This approach, known as methylase selection, was first used successfully by Wilson, EPO Publication No. 0193413, to clone the HaeII, TaqI, BanI, HindIII, HinfI, and MspI R-M systems.

A number of R-M systems, however, have required a multi-step cloning approach. For example, during acquisition of a new R-M system, it has been found that a number of cells face an establishment problem. Unless the methylase has a head start over the endonuclease, the cell is in danger of being restricted. *E. coli* appears to cope with this problem by repairing its DNA, and is able to assimilate to many cloned R-M systems without apparent trauma. Not all systems are easily assimilated however. The DdeI and BamHI R-M systems, for example, could not be cloned in a single step; rather, three steps were required (Howard et al., *Nucleic Acids Res.* 14:7939–7951 (1988)). There are, in fact, many systems for which only the methylase gene has been cloned. These systems may be similar to BamHI and DdeI, and may require similar approaches.

While a number of clones have been obtained by one or more of the above-described methods, see, Wilson, *Gene* 74, 281–289 (1988), cloning of Type II R-M systems is not without difficulty. In particular, the genetics of many R-M systems have been found to be more complex, and methylase positive clones obtained by, for example, vector modification have not yielded the corresponding endonuclease gene. See, Wilson, *Trends in Genetics* 4:314–318 (1988); Lunnen et al., *Gene* 74:25–32 (1988). In fact, numerous obstacles are encountered in the process of cloning R-M systems using vector modification. For example, in some systems, the methylase and endonuclease genes may not be linked or the endonuclease used to fragment the bacterial DNA may cut either or both of the R-M genes. In other systems, such as BamHI and DdeI, the methylase may not protect sufficiently against digestion by the corresponding endonuclease, either because of inefficient expression in the transformation host, or because of the inherent control mechanism for expression of the methylase and endonuclease genes, or for unknown reasons. Modification may also be harmful to the host cell chosen for transformation. The endonuclease sought to be cloned may not be available in sufficient purity or quantity for methylase selection. In many systems, difficulties are also encountered in expressing the endonuclease gene in a transformation host cell of a different bacterial species.

In spite of the difficulties in cloning the more complex Type II R-M systems, it has been possible to obtain some endonuclease genes by modifying the vector modification selection method (see Lunnen et al., op. cit.) and/or by using a multi-step cloning approach. For example, formation of multiple libraries, construction of new cloning vectors, use of isoschizomers for the methylase selection step, mapping of methylase and/or endonuclease genes to determine the corresponding DNA sequences for use as hybridization probes, and other variations to the above-described approaches have yielded a number of recalcitrant recombinant R-M systems.

However, at the outset of any Type II R-M cloning project, one simply does not know which, if any, and what variations or modifications to previous approaches may be required to clone any particular R-M system. For example, the detailed genetics of the particular system is usually unknown. Type II R and M genes may be present on the genome in any of four possible arrangements. Wilson, *Trends in Genetics*, supra. The sizes of the enzymes, and of the corresponding genes, vary widely between one R-M system and another, as do the DNA and amino acid sequences. In fact, isoschizomeric restriction endonucleases have been found to display few similarities. Id, at 318, see also Chandrase-geran et al., *Structure and Expression*, Vol. I, pp 149–156, Adenine Press (1988).

Mechanisms of control of R and M gene expression also vary widely among Type II systems. For example, expression of the endonuclease gene may be modification-dependent, as is indicated in the AvaII, HaeII, HinfI, PstI and XbaI systems (Id.). Alternatively, the endonuclease gene may contain a large number of its own recognition sites as compared to the corresponding methylase gene, as in the TaqI system. Id.

During transformation of cells to obtain clones carrying the target R-M system, cellular DNA is initially unmodified and consequently in danger of being digested by the target endonuclease. Transformation host cells must either contain DNA repair systems or be able to delay expression of the target endonuclease gene until modification is complete. If neither of these mechanisms is available to the transformation host, a problem is encountered in establishing the clones genes in the host. As noted above, when establishment problems were encountered in cloning the DdeI and BamHI systems, it was necessary to introduce the methylase and endonuclease genes sequentially, to protect the DNA of the transformation host cells (Howard, K. A. et al., supra, Brooks et al., *Gene* 74:13 (1988)). However, some R-M systems have resisted all attempts to clone them, and others have yielded only the methylase gene, possibly because of establishment difficulties. Wilson, *Trends in Genetics* 4:317.

It has been found that transformation host cells may also contain systems that restrict foreign types of modification. For example, two systems have been identified in *E. coli* which restrict modified DNAs: the mcr system restricts DNA containing methyl-cytosine, and the mrr system restricts DNA containing methyl-adenine. It is therefore usually necessary to use *E. coli* strains that are defective in these systems. The presence of additional host cell restriction systems may also be responsible for the difficulties encountered in cloning of R-M systems.

Specific Type II restriction endonucleases are already known for numerous DNA sequences, however, a large number of restriction enzymes with diversified enzymatic characteristics are necessary for successful genetic manipulation. Accordingly, there is a continued need for new Type II restriction endonucleases such as the enzyme of the present invention, KasI.

In addition, because restriction endonucleases and modification methylases are useful tools for characterizing and rearranging DNA in the laboratory, there is a commercial incentive to produce the enzymes abundantly and in substantially pure form. Using recombinant DNA techniques in accordance with the present invention, the KasI restriction endonuclease and modification methylase may be produced simply and in commercially useful amounts.

SUMMARY OF THE INVENTION

In accordance with the present invention there is provided a novel restriction endonuclease obtainable from the bacterium *Kluyvera ascorbata*, hereinafter referred to as "KasI", which endonuclease:

(1) recognizes the base sequence in a double-stranded DNA molecule as shown below,

5'-GGCGCC-3'

3'-CCGCGG-5'

(wherein C and G represent cytosine and guanine, respectively), (2) cleaves said sequence in the phosphodiester bonds between G and G as indicated with the vertical arrows; and (3) cleaves double-stranded pUC, M13mp18, and lambda DNA in one position, PhiX172, and T7 DNA in two positions, and Adeno2 DNA at 20 positions, while not cleaving SV40 DNA.

The present invention further provides a recombinant DNA encoding the KasI restriction endonuclease and modification methylase obtainable from *K. ascorbata*, and methods for the production of the recombinant DNA encoding those enzymes. Methods for producing the KasI restriction endonuclease and modification methylase in substantially pure form are also provided.

DETAILED DESCRIPTION OF THE INVENTION

In accordance with the present invention, KasI is obtained by culturing *Kluyvera ascorbata* strain NEB 593 and recovering the enzyme from the cells.

*Kluyvera ascorbata* strain NEB 593 was isolated from a water sample obtained from Keene, New Hampshire in 1988. The sample was returned to New England Biolabs and plated on LB agar and incubated at 30° C. Single colonies were picked and plate purified. Purified samples were assayed for endonuclease activity in accordance with the technique described by Schildkraut in *Genetic Engineering Principles and Methods*, (1984) Setlow, J. K. et al., eds., Plenum Publishing, Vol. 6, pg. 117, the disclosure of which is hereby incorporated by reference. One sample identified as *Kluyvera ascorbata* NEB 593 contained the novel restriction endonuclease KasI.

KasI is an isoschizomer of NarI, and recognizes the palindromic hexanucleotide sequence 5'-GGCGCC-3'. Unlike NarI, KasI cleaves the sequence between the first and second G, generating a 4 base 5' extension.

A sample of *Kluyvera ascorbata* strain NEB 593 was deposited at the American Type Culture Collection (ATCC) on May 25, 1990 and bears Accession No. 55054.

For recovering the enzyme of the present invention, *K. ascorbata* may be grown using any suitable technique, for example, *K. ascorbata* may be grown in a media comprising tryptone, yeast extract and NaCl (pH 7.2), and incubated at 30° C. with agitation and aeration. Cells in the late logarithmic stage are collected using centrifugation and stored frozen at −70° C.

After the cells are harvested and frozen, the enzyme can be isolated and purified from frozen cell paste by using conventional enzyme purification methods. For example, the obtained cell paste is thawed and suspended in a buffer solution and subjected to treatment to allow extraction of the enzyme by the buffer solution, such treatment includes sonication, high pressure dispersion, or enzymatic digestion. The cell residue is then removed by centrifugation, and the supernatant containing the new enzyme can be purified by ion-exchange chromatography, using for example phosphocellulose or DEAE-cellulose, molecular sieve chromatography and affinity chromatography, using for example heparin agarose or DNA-cellulose, or a combination of these methods, to produce the enzyme of the present invention.

The enzyme of the present invention, along with its corresponding DNA methylase may also be obtained using a modified version of the vector modification approach described in EPO Publication No. 0193413.

Figure 1:
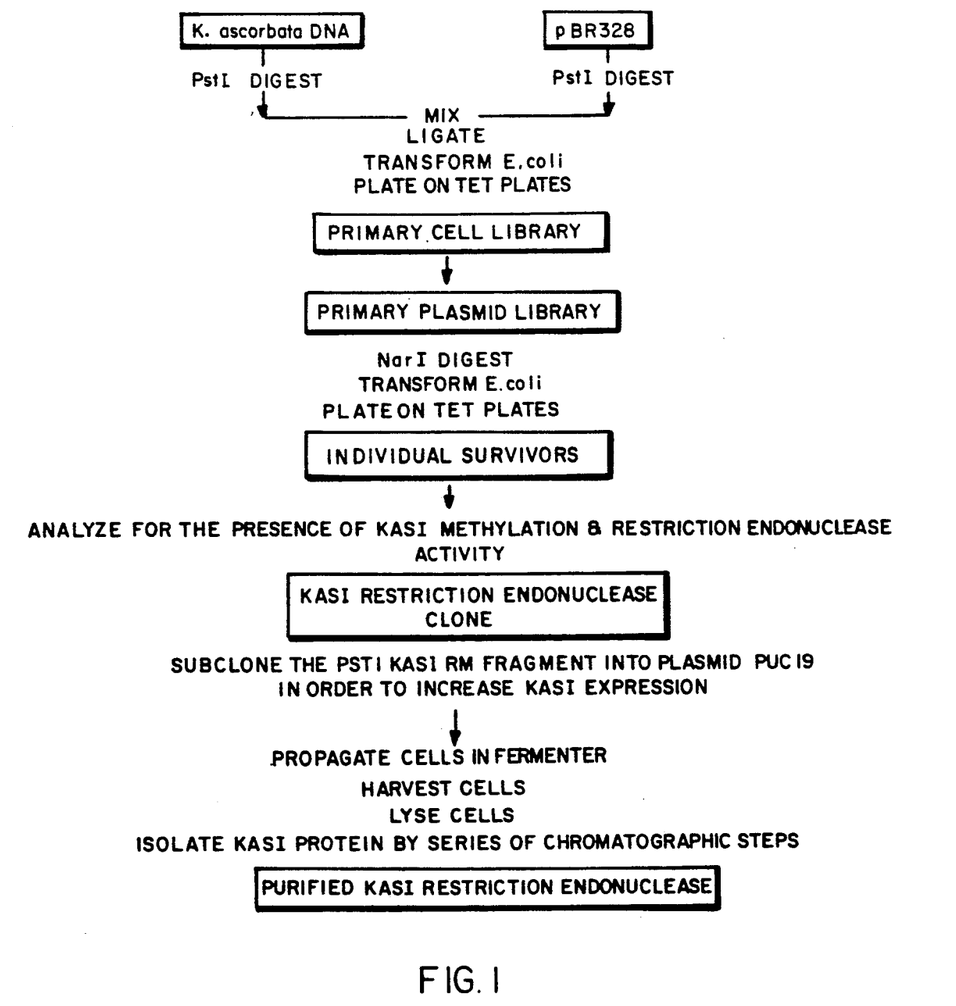
FIG. 1 illustrates the scheme for cloning and producing KasI restriction endonuclease.

The preferred method for cloning recombinant DNA containing the KasI restriction endonuclease and modification methylase genes is generally set forth below, and is represented in FIG. 1.

A. Cloning of KasI Methylase Gene.

The genomic DNA of *K. ascorbata* (ATCC No. 55054) is purified using known methods and partially digested with an appropriate restriction endonuclease. The preferred restriction endonuclease for forming the genomic library of PstI. The digested genomic DNA is then ligated to a cloning vector containing one or more recognition sites which are isoschizomeric to or which contain the recognition sequence of KasI. Since expression of the methylase may be a factor, the cloning vector should have a relatively high copy number. The preferred cloning vector is pBR328; however, other cloning vectors may also be used as long as they contain KasI sites. Such vectors include pBR322, pUC19, and similar plasmids. The ligated DNA is then transformed into an appropriate bacterial host such as *E. coli* RR1 (ATCC No. 31343). Other bacterial hosts which do not restrict the *K. ascorbata* DNA or otherwise interfere with cloning of the methylase gene may also be used. Transformants are selected by plating onto a medium containing an antibiotic or other selection pressure. When pBR328 is used as the cloning vector, for example, the transformants are plated onto Luria agar containing tetracycline.

Recombinant plasmids should be tetracycline resistant and carry inserts of *K. ascorbata* genomic DNA. The tetracycline-resistant colonies are pooled to form the primary cell library. From this pool, recombinant plasmids are purified away from the transformation host's genomic DNA by known methods such as density centrifugation with CsCl and ethidium bromide. The purified recombinant plasmids form the library plasmid library.

The primary plasmid library is then digested to completion with a suitable endonuclease such as KasI or NarI. The KasI recognition site (GGCGCC) is the same as the NarI recognition site. It was found in accordance with the present invention that methylation by the KasI methylase also protects DNA from NarI endonuclease digestion.

Thus, digestion by KasI or NarI endonuclease differentially destroys DNA which has not been modified by the KasI methylase, increasing the proportion of plasmids containing the KasI methylase gene in the primary plasmid library.

The KasI methylase gene-enriched plasmid library is then transformed back into an appropriate bacterial host such as *E. coli* RR1. Transformants are recovered by plating onto a selective medium such as L-agar containing tetracycline. The DNA of surviving colonies is analyzed for the presence of the KasI methylase gene, by digestion with the KasI or NarI endonucleases. This analysis is performed both on purified plasmid DNA and on total cellular (genomic and plasmid) DNA. Clones carrying the KasI modification gene contain fully modified DNA, and both plasmid and genomic DNA is substantially resistant to digestion by KasI and NarI endonucleases.

Clones carrying KasI restriction endonuclease are identified by preparing cell extracts of the KasI methylase clones, obtained above, and assaying the extracts for KasI restriction endonuclease activity.

The quantity of KasI restriction endonuclease produced by the clones may be increased by elevating the gene dosage, through the use of high copy number vectors, such as pUC19, and by elevating the transcription rate, through the use of highly active, exogenous promoters.

B. Production of Recombinant KasI Endonuclease and Methylase.

Recombinant KasI restriction endonuclease and methylase may be produced from clones carrying the KasI restriction and modification genes by propagation in a fermenter in a rich medium containing the appropriate antibiotic. The cells are collected by centrifugation and disrupted by sonication to produce a crude cell extract containing the KasI restriction endonuclease activity.

The crude cell extract containing the KasI restriction endonuclease and/or methylase activity is purified by standard protein purification techniques such as affinity chromatography and ion-exchange chromatography.

Although the above-outlined steps represent the preferred mode for practicing the present invention, it will be apparent to those skilled in the art that the above-described approach can vary in accordance with techniques known in the art.

The recognition sequence of the endonuclease sequence of the present invention, KasI, can be determined by digesting pUC19, pBR322, phiX174, M13mp18, SV40, T7, lambda, and Adeno2 DNA with the restriction enzyme of the present invention and using agarose gel electrophoresis to determine the number and sizes of the fragments thus generated. The number and sizes the fragments generated by digestion with KasI for the 8 DNA molecules above (31 sites) match the computer-predicted (Devereaux, et al., NAR 12, 387–395 (1984)), number and sizes of the fragments that would be generated by cleavage at the sequence 5'-GGCGCC-3'. KasI has the following number of recognition sequences on the DNAs listed above: pUC19 (1), pBR322 (4), phiX174 (2), M13mp18 (1), SV40 (0), T7 (2), lambda (1), and Adeno2 (20). From the above data, it was concluded that KasI recognizes the sequence 5'-GGCGCC-3', and thus is an isoschizomer of NarI.

The point of cleavage on the recognition sequence of the endonuclease of the present invention can be determined by using dideoxy sequencing (Sanger, F., et al., *PNAS* (1977) 74:5463–5467), to analyze the terminal base sequence obtained by cleaving pUC19 with the enzyme of the present invention. Using the technique described-above, and further exemplified in Example III, it was concluded that the KasI cleavage position is between the first and second nucleotides, G and G, in its recognition sequence which results in a 5'4-base extension as shown below, and wherein the cleavage position is defined with the vertical arrows.

The following examples are given to illustrate embodiments of the present invention as it is presently preferred to practice. It will be understood that these examples are illustrative, and that the invention is not to be considered as restricted thereto except as indicated in the appended claims.

EXAMPLE I

Isolation and Purification of Native KasI

*Kluyvera ascorbata* strain NEB 593 (ATCC No. 55054) was grown in a 500 ml culture of Luria Broth (tryptone, yeast extract and NaCl (pH 7.2)) overnight at 30° C. with agitation and aeration. Cells in the late logarithmic stage were collected using centrifugation and stored frozen at −70° C.

The enzyme KasI was isolated and purified from the frozen cell paste of *Kluyvera ascorbata* using the following enzyme purification method. The *K. ascorbata* frozen cell paste was thawed and suspended in a buffer A (20 mM Tris, pH 7.4, 10 mM magnesium chloride, 1 mM β-mercaptoethanol, and 0.1 mM EDTA), and subjected to sonication treatment to allow extraction of the enzyme by the buffer solution. The cell residue was then removed by centrifugation, and the supernatant was assayed (50 mM NaCl, 10 mM Tris, 10 mM magnesium chloride, 1 mM β-mercaptoethanol) at 37° C. for one hour for endonuclease activity on lambda and T7 DNAs, in accordance with the technique described by Schildkraut in *Genetic Engineering Principles and Methods*, (1984) Setlow, J. K., et al., eds., Plenum Publishing, Vol. 6, pg. 117. The enzymatic activity detected (positive on both lambda and T7 DNAs) in the supernatant was isolated and purified using a 1 ml bed volume heparin-sepharose affinity chromatography column with a 50 ml linear gradient from 50 mM NaCl to 1 M NaCl in Buffer A. 1.5 ml fractions from the heparin-sepharose column were assayed (50 mM NaCl, 10 mM Tris pH 7.4, 10 mM magnesium chloride, 1 mM β-mercaptoethanol), at 37° C. for one hour on T7 DNA, and a broad peak of KasI activity was located (fractions 11–21). The enzyme obtained, fraction 19, was substantially pure.

EXAMPLE II

Cloning of KasI Restriction Endonuclease and Methylase Genes

1. DNA purification: A frozen glycerol culture of *Kluyvera ascorbata* cells was obtained. A dollop of frozen cells were streaked onto a LB plate and incubated overnight at 37° C. A single colony was inoculated and cultured in 1 liter of L-Broth overnight at 37° C. The cells were pelleted and frozen. The pellet was defrosted at room temperature and suspended in 50 ml of 5 mM Glucose, 2.5 mM Tris (pH 8.0), 1.0 mM EDTA containing 10 mg/ml lysozyme. The suspension was shaken at 30° C. for 1 hour. SDS was added to a final concentration of 1% and shaken for 1 hour. One mg/ml proteinase K was added and shaken for 1 hour at 37° C. The mixture was forced through an 18 gauge needle and extracted with an equal volume of phenol and chloroform. The solution was shaken and spun at about 10 krpm for approximately 10 minutes. The aqueous phase was removed and the aqueous phase was re-extracted with chloroform. The aqueous phase was removed and dialyzed against 16 liters of 1× DNA buffer (10 mM Tris pH 8.0, 1 mM EDTA) over the course of 24 hours.

The dialyzed solution was then digested with RNAse at a final concentration of 200 ug/ml for 1 hour at 37° C. The DNA was then precipitated by the addition of 5M NaCl to a final concentration of 0.4M, and 0.55 Volumes of isopropyl alcohol. The precipitated DNA was spooled onto a glass rod, air-dried, then dissolved in a DNA buffer to a concentration of approximately 200 ug/ml and stored at 4° C.

2. Digestion of DNA: 12 ug of *Kluyvera ascorbata* DNA was diluted into 600 ul of HindIII restriction endonuclease digestion buffer (10 mM Tris pH 7.5, 10 mM MgCl$_2$, 10 mM mercaptoethanol, 50 mM NaCl). Five tubes were prepared the first containing 200 ul of buffer and DNA. Each subsequent tube contained 100 ul of buffer and DNA. 20 units of PstI restriction endonuclease were added to the first tube. The tube was mixed and 100 ul transferred to the second tube in order to serially dilute the enzyme. The solution was incubated at 37° C. for 1 hour. An aliquot from each tube was run on a gel to determine the degree of digestion. Tubes were combined and extracted with phenol/-chloroform and chloroform and precipitated with the addition of NaCl to 0.4M and 0.55 volumes of isopropanol.

Additional libraries were prepared by digesting the KasI chromosomal DNA with EcoRI, HindIII, BamHI, BglII, or NsiI as described above.

3. Ligation and transformation: 2 ug of PstI-digested *Kluyvera ascorbata* DNA was mixed with 1 ug of PstI-cleaved and dephosphorylated pBR328 (ATCC No. 37517) 10 ul of 10X ligation buffer (500 mM Tris pH 7.5, 100 mM MgCl$_2$, 100 mM DTT, 5 mM ATP), and 55 ul of sterile distilled water were added and the solution was incubated at room temperature for 30 minutes and 16° C. overnight. 100 ul of the ligation solution was mixed with 1 ml of SSC/CaCl$_2$ (50 mM NaCl, 5 mM Na$_3$Citrate, 67 mM CaCl$_2$ and 2 ml of ice-cold, competent *E. coli* RR1 (ATCC No. 31343) cells were added. The solution was incubated at 42° C. for 3 mins, then 5 ml of Luria-broth was added and incubation was continued at 37° C. shaker for 3 hr.

The same procedure was applied for making the EcoRI, HindIII, NsiI and BamHI libraries.

4. Cell Library: The transformed culture was gently centrifuged, the supernatant was discarded and the cells were resuspended in 1.0 ml of L-broth. 200 ul portions of the resuspended cells were plated onto Luria-agar (L-agar) plates containing 30 ug/ml tetracycline. The plates were incubated at 37° C. The transformed cells that grew up on the surfaces of the plates were collected together by flooding each of the plates with 2.5 ml of 10 mM Tris pH 7.5, 10 mM MgCl$_2$, scraping the colonies together, and pooling the suspensions into a single tube.

5. Plasmid Library: 5.0 ml of the cell library was inoculated into 500 ml of L-broth containing 30 ug/ml tetracycline. The culture was shaken overnight at 37° C. then centrifuged at 4K rpm for 5 minutes. The supernatant was discarded and the cell pellet was resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris pH 8,0 were added. The solution was kept on ice for 1 hour, then 12 ml of 1% Triton X-100, 50 mM Tris pH 8.0, 67 mM EDTA was added and the suspension was gently swirled to induce cell lysis.

The lysed mixture was transferred to a 50 ml tube and centrifuged for 45 min. at 17K rpm, 4° C. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10 mM Tris pH 8.0, 100 mM NaCl, 1 mM EDTA was added. The solution was transferred to two ⅝ in. ×3 in. centrifuge tubes and spun in a Beckman Ti70 rotor for 42 hours at 44K rpm, 17° C. To collect the plasmids, the tubes were opened, illuminated with ultraviolet light, and the lower of the two fluorescent bands was collected by syringe. The lower band from each tube was combined and the ethidium bromide was removed by extracting four times with an equal volume of water-saturated, ice-cold N-Butanol.

The extracted solution was dialyzed against 16 liters (4 changes over 24 hours) of 1× DNA buffer, then the nucleic acid was precipitated by the addition of 2 vols. of isopropanol and sufficient 5M NaCl to reach a final concentration of 0.4M. The solution was stored overnight at −20° C. then centrifuged for 15 minutes at 15K rpm, 0° C. The supernatant was discarded, the pellet was air-dried for 15 min. then dissolved in 250 ul of 10 mM Tris pH 7.5, 1 mM EDTA and stored at −20° C.

The plasmid DNA concentration was found to be approximately 200 ug/ml.

6. Digestion of the Plasmid Library: 25 ug (25 ul) of the plasmid library was diluted into 770 ul of NarI endonuclease (NarI is an isoschizomer of KasI and was used to select methylase clones from KasI libraries) digestion buffer (10 mM Tris pH 7.5, 10 mM MgCl₂, 10 mM mercapteothanol, 10 mM NaCl). The mixture was dispensed into 4 tubes containing 200 ul each. A serial titration of the NarI enzyme was made by adding 40 units of the enzyme to the first tube and removing 50 ul and mixing it with the second tube. The dilution procedure continued through the subsequent tubes. The titration series was incubated at 37° C. for 1 hr. 25 ul of the reaction was run on a gel, the remainder of first tube was transformed into *E. coli* RR1 (ATCC No. 31343) while the remainder of the other tubes was frozen at −20° C.

7. Transformation: Approximately 50 ul (∼1.5 ug) of the digested library was mixed with 100 ul of SSC/CaCl₂ (section 3) and 200 ul of ice-cold, competent, *E. coli* RR1 . The mixture was heat shocked at 42° C. for 3 minutes. The cell pellet was resuspended in 150 ul of L-broth and plated onto an L-agar containing 30 ug/ml tetracycline. The plate was incubated overnight at 37° C. NarI digestion reduced the number of transformants $10^3$-fold compared with transformation by undigested plasmids. Ten colonies were picked from the survivors of the NarI digestion; each was inoculated into 10 ml of L-broth containing tetracycline, to prepare a miniculture, and streaked onto an L-agar plate containing tetracycline, to prepare a master stock.

8. Analysis of surviving individuals: 10 of the surviving colonies obtained from section 7 were grown into 10 ml cultures and the plasmids that they carried were prepared by the following miniprep purification procedure, adapted from the method of Birnboin and Doly, *Nucleic Acids Res.* 7:1513 (1979).

Miniprep Procedure: Each culture was centrifuged at 5–7K rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15K rpm, 4° C. for 10 minutes. Each supernatant was poured into a centrifuge tube containing 3 ml of isopropanol and mixed. After 10 minutes at room temperature, the tubes were spun at 15K rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA, pH 8.0 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5m NaCl followed by 350 ul of isopropanol. After 10 minutes at room temperature, the DNA was spun down by centrifugation for 45 seconds, the supernatants were discarded and the pellets were redissolved in 150 ul of 10 mM Tris 1 mM EDTA, pH 8.0. The plasmid minipreps were subsequently analyzed by digestion with NarI and PstI.

Figure 2:
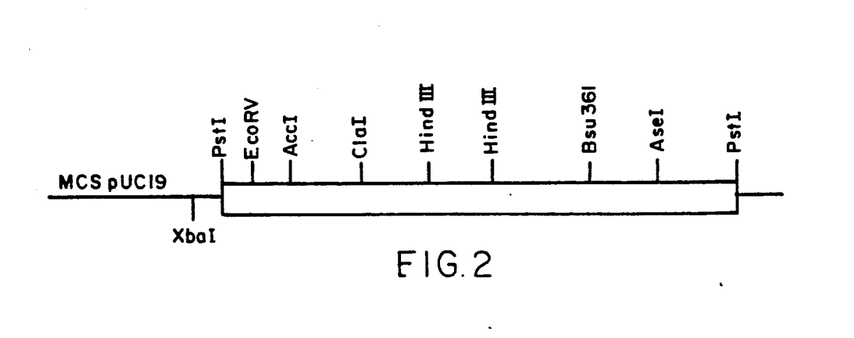
FIG. 2 is a restriction map of a 3.4 kb PstI fragment of *Kluyvera ascorbata* DNA that encodes the KasI restriction endonuclease and modification methylase. The fragment was cloned into the PstI site of pUC19 (ATCC 37254) to create pJBKasIRM 104-12.

9. KasI Methylase Gene Clones: All of the 10 plasmids that were analyzed were found to be resistant to NarI digestion and to carry at least a 3.4 kb fragment of *Kluyvera ascorbata* DNA. The simplest clone, carrying only the 3.4 kb fragment, was mapped by restriction enzyme digests (FIG. 2). This plasmid (pJB1911RM 604–4) was found not only to encode the KasI methylase but the KasI restriction endonuclease as well.

The EcoRI and NsiI libraries yielded methylase clones as well. None of the EcoRI methylase clones contained the endonuclease gene but 3 different classes of the NsiI methylase clones contained the endonuclease gene and expressed activity. The PstI 3.4kb clone was chosen to pursue because it expressed the most KasI activity and was the simplest construct.

10. KasI Restriction Gene Clone: pJB1911RM 604–4, and similar plasmids, were found to encode and express the KasI restriction endonuclease by assaying extracts of *E. coli* RR1 that carried the plasmids.

Endonuclease Assay: A 100 ml culture of the cells to be assayed was grown overnight at 37° C. in L-broth containing 30 ug/ml tetracycline. The culture was centrifuged at 4K rpm for 5 min and the cell pellet was resuspended in 3.5 ml of 10m KPO₄ pH 7.5, 10 mM mercaptoethanol, 0.1 mM EDTA. 0.5 ml of 10 mg/ml lysozyme in the same buffer was added and the suspension was left on ice for 2 hr. The suspension was frozen at −20° C., then thawed on ice. 1.0 ml of the thawed suspension was sonicated gently for three 10-second bursts to disrupt the cells. The sonicated extract was microcentrifuged for 5 minutes to remove cell debris and the supernatant was assayed for endonuclease activity in the following way:

60 ug (85 ul) of purified phage lambda DNA was diluted into 1200 ul of NarI restriction endonuclease digestion buffer (section 6). The solution was dispensed into 6 tubes, 150 ul into the first tube and 100 ul into each of the remaining 5 tubes. 7.5 ul of the extract was added to the first tube to achieve 1 ul extract/ug DNA. 50 ul was then removed form the first tube and transferred to the second tube to achieve 0.3 ul/ug. 50ul serial transfers were continued into tubes 3 (0.1 ul/ug), 4 (0.03 ul/ug) and 5 (0.001 ul/ug). The sixth tube received no extract and served as a negative control. The tubes were incubated at 37° C. for one hour, then 20 ul from each was analyzed by gel electrophoresis. The extract was found to contain approximately $1 \times 10^4$ units of KasI restriction endonuclease per ml, which corresponds to about $1 \times 10^5$ units per gram of cells.

Figure 3:
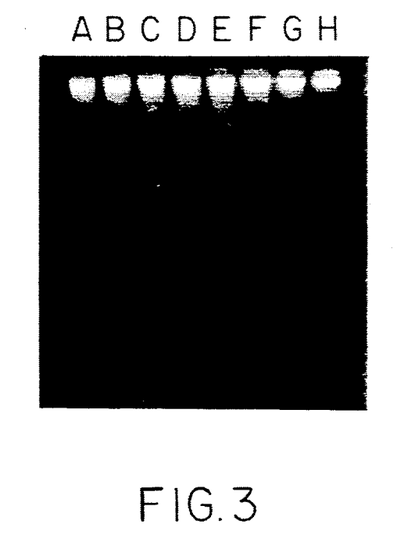
FIG. 3 is a photograph of an agarose gel demonstrating KasI restriction endonuclease activity, in cell extracts of *E. coli* strain NEB 594 (ATCC No. 68353) carrying pJBKasIRM 104-12. An overnight culture of 8 mls of cells with antibiotic, was pelleted, and resuspended in sonication buffer. The cells were broken by sonication and the cell debris pelleted. One μl of the crude supernatant was titrated in an assay on 50 ug/ml lambda DNA for one hour at 37° C.

11. Transfer of the 3.4 kb fragment to pUC19: Ten micrograms of the pJBKasIRM 604–4 plasmid was digested with about 100 units of PstI endonuclease for about 5 hours at 37° C. The digest was loaded onto a 1% agarose gel and run overnight at 25 milliamps. The following morning the bands were visualized with a UV lamp and the 3.4 kb band was excised from the gel. The excised piece was passed through an 18 gauge needle and suspended in 1× DNA buffer. The agarose was pelleted by centrifugation for 30 minutes at 15K rpm and the supernatant was poured off immediately. The supernatant was extracted with an equal volume of phenol:chloroform (1:1) followed by an extraction with an equal volume of chloroform. The aqueous phase was precipitated by the addition of salt to a final concentration of 0.4M and 2 volumes of isopropanol. The fragments were precipitated overnight at −20° C. then pelleted by centrifugation of 15Krpm for 30 minutes. The fragments were air dried briefly and resuspended in 1× DNA buffer. Approximately 0.5 ug of fragments were ligated to 1 ug of PstI linearized pUC19 and transformed into *E. coli* RR1 and plated on ampicillin. The plates were incubated at 37° C. overnight. Fourteen colonies were picked from nearly 1000 colonies that had grown up on the plates. These colonies were miniprepped (as discussed earlier) in order to examine their DNA. Twelve of the 14 colonies contained the 3.4 kb fragment and were resistant to NarI digestion. One-half of the colonies that were miniprepped were normal in their morphology on the plate, the other half were abnormal, two colonies were looked at in more detail: clone #8 was abnormal and #12 was normal. Clone #8 expressed slightly greater KasI activity than #12 and was shown to have the 3.4 kb PstI fragment in an opposite orientation to #12. Clone #12 was used for further assays and was determined to have nearly $10^6$ units per gram of cells of KasI (when assayed on lambda DNA, see FIG. 3) which is about 3-5 times more activity than in the pBR328 plasmid. This clone, NEB 594, pJBKasIRM 104-12 transformed into *E. coli* RR1, was used for future extraction and characterization of KasI.

A sample of *E. coli* strain NEB 594 was deposited at the American Type Culture Collection (ATCC) on Jul. 3, 1990 and bears Accession No. 68353.

EXAMPLE III

Determination of the KasI Cleavage Site

Figure 4:
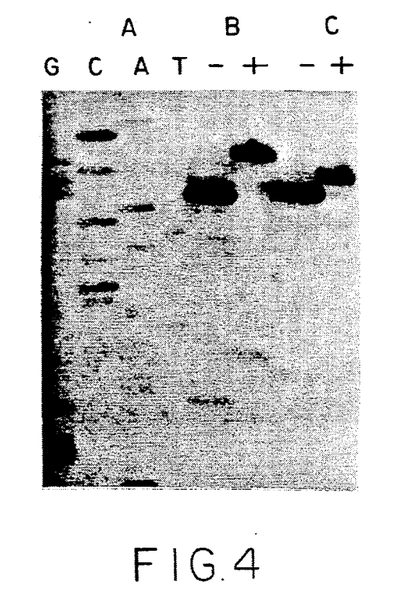
FIG. 4 is an autoradiograph of a polyacrylamide sequencing gel illustrating the cleavage site determination for KasI.

The cleavage site of the KasI restriction endonuclease was determined using extract from NEB 594(ATCC No. 68353), obtained in Example II. A plasmid (pUC19) was obtained containing a single KasI/NarI site. An oligonucleotide sequencing primer was made approximately 50 bp 5′ from the KasI/NarI site. The plasmid was prepared for double stranded sequencing by denaturing with alkali, neutralizing and precipitating the denatured plasmid. The primer was annealed to the plasmid by incubating at 37° C. for 30 minutes. Five units of Klenow and 10 microcuries of alpha-$^{35}$S-dATP were added to the reaction mixture. The reaction was split in half: reaction A continued as a standard sequencing reaction, while reaction B was used to form a "hot strand" to determine the site at which KasI cleaves. "A" diluent which contains equimolar amounts of C, T, and G was added to reaction B and incubated for 30 minutes at 37° C. Chase dNTPs were added to the reaction mix and incubated for 30 minutes at 37° C. The Klenow was heat killed at 70° C. for 25 minutes. KasI enzyme was added to the reaction mix and incubated at 37° C. for 30 minutes. The B reaction was split into two tubes: A minus tube to which 5 ul of stop buffer was added and a plus tube to which 0.5 ul (2.5 U) of Klenow was added. The plus tube was incubated at room temperature for 15 minutes and the reaction was terminated by the addition of 5 ul of stop buffer. A third reaction, reaction C was carried out similarly to reaction B except NarI was substituted for KasI to cleave the DNA. The (A) standard sequencing reaction was run along side the (B) KasI reaction (−/+) and the (C) NarI reaction (−/+) on a 6% 0.4–0.8mm polyacrylamide sequencing gel. The results show that KasI cuts the sequence 5′GCGCGCC and NarI cuts the sequence 5′GGCGCC (refer to FIG. 4).

EXAMPLE IV

Purification of Recombinant KasI

*E. coli* strain NEB 594 (ATCC NO. 68353) was grown in LB media consisting of 10 g/l tryptone, 5 g/l yeast extract, 10 g/l NaCl (adjusted to pH 7.5), supplemented with ampicillin. The cells were incubated at 37° C. until late logarithmic stage with aeration and agitation. The cells were harvested by centrifugation and stored frozen at −70° C. 594 grams of the cells obtained were suspended in 1188 ml of buffer A, (10 mM KPO$_4$ pH 7.0, 10 mM EDTA, 0.05 M NaCl and 10 mM 2-mercaptoethanol) and broken in a Gaulin press to an O.D. 260 of 1.4 (1:300 dilution). The suspension was then spun in a Sharples centrifuge and 1000 ml of cleared lysate was recovered.

The lysate obtained was layered over a 5×20 cm column containing 350 ml of Affi-Gel Blue (Biorad) equilibrated in buffer A, washed with 400 ml of buffer A and eluted with a 1400 ml NaCl gradient to 1 M. 15 ml fractions were collected and assayed for restriction endonuclease activity by incubating 1 ul of sample in 50 ul of 10 mM Tris pH 7.5, 10 mM MgCl, 1 mM dithiothreitol, 1 ug/ml HindIII digested lambda DNA for 5 minutes at 37° C. Cleaved DNA was visualized on a 1% agarose gel. The fractions containing KasI restriction endonuclease activity eluted at a NaCl concentration of 0.45 M and were pooled (total volume 650 ml).

The pooled activity was dialyzed against Buffer A overnight and then layered over a 2.5×15 cm column containing 75 ml heparin Sepharose (Pharmacia) equilibrated in Buffer A, washed with 150 ml of Buffer A and eluted with 400 ml NaCl gradient to 1 M. 3 ml fractions were collected and assayed in the same manner as above. The fractions possessing KasI restriction endonuclease activity eluted at an NaCl concentration of 0.35 M and were pooled (40 ml volume).

The pooled fractions were concentrated using a Amicon pressure filtration device to a final volume of 10 ml and then placed on top of a 2.5 cm×1.5 m G75 column (Pharmacia) equilibrated in Buffer A+0.5 M NaCl. 7.5 ml fractions were collected and assayed as above. The fractions with KasI restriction endonuclease activity eluted off the column at 250 ml and were pooled (total volume 46 ml).

The pooled fractions were dialyzed against Buffer A overnight and loaded on a 1 ml Mono-Q FPLC column (Pharmacia) equilibrated in Buffer A. A 100 ml NaCl gradient to 1 M was run and 1 ml fractions were collected and assayed as above. The enzyme activity eluted in a sharp 3 ml peak at 0.32 M NaCl.

The purified enzyme was diluted with 3 ml of glycerin for storage purposes for a total volume of 6 ml.

Restriction enzyme purity was determined by the following methods: 95% of the HindIII cut lambda DNA fragments produced by a 50-fold over-digestion of KasI in Buffer B was ligated with T4 DNA ligase (at a 5′ termni concentration of 1–2 uM at 16° C.). Of these ligated fragments, 95% were recut by KasI. A 50 ul reaction containing 1 ug of HindIII cut lambda DNA and 50 units of KasI incubated for 16 hours in 10 mM Tris pH 7.5, 10 mM MgCl, 1 mM dithiothreitol, resulted in the same pattern DNA bands as a reaction produced in one hour with one unit of KasI. Incubation of 40 units of KasI for 4 hours at 37° C. in 50 ul 10 mM Tris pH 7.5, 10 mM MgCl, 1 mM dithiothreitol, with 1 ug sonicated $^3$H DNA ($10^5$ cpm/ug) released 0.08% radioactivity measured as TCA acid soluble counts.

What is claimed is:

1. A substantially pure Type II restriction endonuclease obtainable from *Kluyvera ascorbata* ATCC No. 55054 recognizing the following base sequence in double-stranded deoxyribonucleic acid molecules:

5'-G↓GCGCC-3'

3'-CCGCG↑G-5' and having a cleavage position defined by the arrows.

2. The Type II restriction endonuclease of claim 1, cleaving double-stranded deoxyribonucleic acid pUC19, M13mp18, and lambda in one position.

3. The Type II restriction endonuclease of claim 1, wherein the restriction endonuclease is purified from *K. ascorbata* (ATCC No. 55054).

4. A substantially pure recombinant restriction endonuclease KasI which recognizes the following base sequence in double-stranded deoxyribonucleic acid molecules:

5'-G↓GCGCC-3'

5'-CCGCG↑G-5' and having a cleavage position defined by the arrows, which endonuclease is a) obtainable from *K. ascorbata* ATCC No. 55054, and, b) free of non-specific endonuclease and exonuclease activity.

5. The restriction endonuclease of claim 1, wherein said endonuclease is isolated from a recombinant organism transformed with a vector that codes for the expression of KasI endonuclease.

* * * * *